United States Patent [19]

Graham et al.

[11] Patent Number: 4,812,463

[45] Date of Patent: Mar. 14, 1989

[54] ALKANESULFONAMIDES AS ANTIGLAUCOMA AGENTS

[75] Inventors: Samuel L. Graham, Harleysville; Thomas H. Scholz, Souderton, both of Pa.

[73] Assignee: Merck & Co., Inc., Rahway, N.J.

[21] Appl. No.: 131,486

[22] Filed: Dec. 10, 1987

Related U.S. Application Data

[63] Continuation of Ser. No. 880,535, Jun. 30, 1986, abandoned.

[51] Int. Cl.$^4$ ................. A61K 31/47; A61K 31/64; C07C 143/72; C07C 433/02
[52] U.S. Cl. .................................... 514/311; 514/357; 514/400; 514/445; 546/136; 546/338; 548/342; 549/65; 564/84; 564/89; 564/98
[58] Field of Search ............... 549/65; 546/136, 338; 548/342; 564/84, 89, 98; 514/311, 357, 445, 400, 601, 604

[56] References Cited

U.S. PATENT DOCUMENTS

| | | | |
|---|---|---|---|
| 3,501,578 | 3/1970 | Schlor et al. | 424/321 |
| 3,862,184 | 1/1975 | Goralski et al. | 260/247.1 |
| 3,862,935 | 1/1975 | Goralski | 260/246 B |
| 3,865,822 | 2/1975 | Goralski et al. | 260/247.1 |
| 3,895,010 | 7/1975 | Goralski et al. | 260/247.1 |
| 3,946,007 | 3/1976 | Goralski et al. | 260/247.1 |
| 4,628,109 | 12/1986 | Schmidt et al. | 560/13 |
| 4,650,902 | 3/1987 | Bender et al. | 564/80 |
| 4,691,056 | 9/1987 | Gunther | 564/96 |
| 4,721,794 | 1/1988 | Shepard et al. | 549/65 |

*Primary Examiner*—Anton H. Sutto
*Attorney, Agent, or Firm*—William H. Nicholson; Michael C. Sudol, Jr.

[57] ABSTRACT

Alkane sulfonamides with an electron withdrawing function $\beta$ to the sulfonamide group are topically effective carbonic anhydrase inhibitors useful in the treatment of elevated intraocular pressure and glaucoma.

10 Claims, No Drawings

ALKANESULFONAMIDES AS ANTIGLAUCOMA AGENTS

This is a continuation of application Ser. No. 880,535, filed June 30, 1986, now abandoned.

SUMMARY OF THE INVENTION

This invention is concerned with novel alkanesulfonamides of general structural formula:

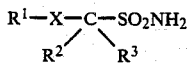

wherein X is —CO—, —SO— or —SO$_2$— which are carbonic anhydrase inhibitors useful in the treatment of elevated intraocular pressure.

This invention is also concerned with pharmaceutical, especially topical ophthalmic formulations which are useful in the novel method of this invention for the treatment of elevated intraocular pressure, especially when accompanied by pathological damage such as in glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

Additionally, U.S. Pat. No. 4,544,667 discloses a series of benzofuran-2-sulfonamides.

It has generally been believed that carbonic anhydrase inhibitory activity was manifested only by aromatic sulfonamides, but now, with this invention there is provided a new class of carbonic anhydrase inhibitors which are (substituted alkane) sulfonamides.

DETAILED DESCRIPTION OF THE INVENTION

The novel compound of this invention has structural formula:

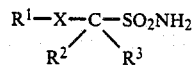

wherein
X is

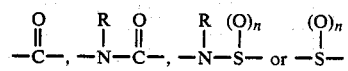

wherein
R is hydrogen or C$_{1-3}$ alkyl; and
n is 0, 1 or 2;
R$^1$ is
(a) carbocyclic or heterocyclic aromatic such as phenyl, naphthyl, pyridyl, thienyl, imidazolyl or quinolinyl either unsubstituted or substituted with one or more of:
 (i) —OR$^4$ wherein R$^4$ is hydrogen C$_{1-3}$ alkyl, or C$_{2-4}$ alkanoyl,
 (ii) halo, such as chloro, bromo or fluoro,
 (iii) R$^5$, which is C$_{1-5}$ alkyl, either straight branched or cyclic, and either unsubstituted or substituted with one or more of —OR$^4$
 (iv)

with the proviso that R$^1$—X— cannot represent benzoyl;
(b) C$_{1-8}$ alkyl either straight chain branched chain or cyclic, and either unsubstituted or substituted with
 (i) —OR$^4$,
 (ii) halo, such as chloro, bromo, or fluoro, or
 (iii) carbocyclic or heterocyclic aromatic such phenyl, naphthyl, pyridyl, thienyl, imidazolyl or quinolinyl, either unsubstituted or substituted with:
  (1) OR$^4$
  (2) halo such as chloro, bromo or fluoro, or
  (3) R$^5$;
R$^2$ and R$^3$ are independently,
 (a) hydrogen, or (b) halo, such as chloro, bromo or fluoro; and
$R^1$ and $R^3$ can be joined together to form a 5- or 6-membered ring.

A preferred embodiment of the novel compounds is that wherein X is $SO_2$, $R^1$ is $C_{1-8}$ alkyl, and $R^2$ and $R^3$ are independently hydrogen or halo, especially chloro.

A process for preparing compounds of this invention wherein X is $-SO_2-$ comprises oxidation of the corresponding thio compound with a suitable oxidizing agent such as Oxone$^R$, or a per-acid such as meta-chloroperbenzoic acid. The latter is used in an inert organic solvent such as a chlorinated hydrocarbon, such as methylene chloride at about 40° to reflux temperature for about 8 to 36 hours. Oxone$^R$ is generally employed in aqueous alcoholic solutions at about 15° to 30° C. for about 0.5 to 4 hours.

Thio-ethers forming a part of this invention are prepared by condensing a mercaptan with an alkyl or aryl halide, especially bromide.

Acyl compounds such as alkanoyl compounds are prepared from alkanoyl chlorides or anhydrides and an alcohol or an amine by standard procedures. Similarly sulfonyl chlorides and ammonia provide sulfonamides by standard procedures.

Sulfonamides are also preparable by treatment of lithium sulfinates with hydroxylamine O-sulfonic acid in aqueous medium at about 5°–25° C. for about 8 to 24 hours.

The novel pharmaceutical formulations of this invention are adapted for oral administration such as tablets, capsules or the like; for nasal administration, especially in the form of a spray; for injection, in the form of a sterile injectable liquid; or for topical ocular administration in the form of solutions, ointments or solid water soluble polymeric inserts.

This invention is particularly concerned with formulations adapted for topical ocular administration for the treatment of glaucoma and other stages of elevated intraocular pressure and contain about 0.1% to 15% by weight of medicament, especially about 0.5% to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

2,3-Dihydro-6-methoxy-2-sulfamoylbenzo[b]thiophene-1,1-dioxide

Step A: Preparation of 6-methoxy-2-sulfamoylbenzo[b]thiophene-1,1-dioxide

A mixture of 2.36 g (9.7 mmol) of 6-methoxy-2-sulfamoylbenzo[b]thiophene, 4.6 g (21.3 mmol) m-chloroperbenzoic acid (80%) and 25 ml of methylene chloride was heated at reflux for 15 hours. After cooling, the mixture was diluted with sufficient ethyl acetate to dissolve the precipitate. The solution was washed with ice-cold water, 80 ml of ice-cold 5% (w/v) sodium bicarbonate, dilute hydrochloric acid and brine, dried and evaporated to dryness. The residue was slurried in 200 ml of ether and collected on a filter to give 2.0 g (75%) of product.

Step B:
2,3-Dihydro-6-methoxy-2-sulfamoylbenzo[b]thiophene-1,1-dioxide

The product from Step A (200 mg) was dissolved in 1.5 ml of DMSO and was added rapidly dropwise to a solution of 200 mg of $NaBH_4$ in 5 ml of 95% ethanol. After 30 minutes, the mixture was poured into dilute HCl and extracted with ethyl acetate. The extract was washed with water, and brine and dried ($Na_2SO_4$) and evaporated to dryness. The residue was pure by TLC and the structure was not contraindicated by $^1$H-NMR. Mass spectrum shows m/e=277. Calc'd for $C_9H_{11}NO_5S_2$: C, 38.98; N, 5.05; H, 4.00%. Found: C, 39.34; N, 5.15; H, 3.95%.

EXAMPLE 2

4-bromophenylthiomethanesulfonamide

A suspension of 1.4 g of a 60% sodium hydride/oil dispersion was prepared in 10 ml of dry DMSO, under an atmosphere of nitrogen. 4-Bromothiophenol (6.5 g) was dissolved in 11 ml of dry DMSO and added slowly to the above suspension. When frothing had subsided 6.0 g of bromomethanesulfonamide was added and the reaction mixture was heated to 80° C. for 2 hours. The reaction mixture was cooled to room temperature and poured into 150 ml of ethyl acetate, filtered from a solid and extracted with brine. The organic phase was dried over anhydrous sodium sulfate and concentrated under vacuum. The resultant residue was recrystallized from toluene to yield 7.9 g (81.4%) of product.

Employing the procedure substantially as described in Example 2, but substituting for the 4-bromophenylthiophenol, the mercaptans described in Table I, there were prepared the thiomethanesulfonamides also described in Table I in accordance with the following reaction scheme:

TABLE I $$R^1-SH + Br-\underset{R^2}{\underset{|}{C}}-SO_2NH_2 \longrightarrow R^1-\underset{R^2}{\underset{|}{S}}-\underset{R^3}{\underset{|}{C}}-SO_2NH_2$$

| $R^1$ | $R^2$ | $R^3$ | m.p. (°C.) |
|---|---|---|---|
| 4-HOC$_6$H$_4$— | H | H | 140–141 |
| 4-CH$_3$OC$_6$H$_4$CH$_2$— | H | H | 93.0–94.5 |
| C$_6$H$_5$CH$_2$CH$_2$— | H | H | 69–70 |
| C$_6$H$_5$(CH$_2$)$_3$— | H | H | 87–88 |
| 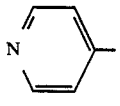 | H | H | 165–166 |
| 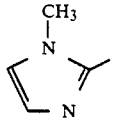 | H | H | 117–119 |
| n-C$_8$H$_{17}$— | H | H | 91.5–93.5 |

EXAMPLE 3

4-bromophenylsulfonylmethanesulfonamide

4-Bromophenylthiomethanesulfonamide (7.9 g) was dissolved in 300 ml of warm methanol. An aqueous solution of 34.4 g of Oxone$^R$ was added gradually. After stirring for one hour the reaction mixture was cooled to ice bath temperature and the precipitated solid was collected on a filter. Yield 7.3 g (83.0%); NMR (DMSO-d$_6$, 90 MHz) δ 5.16 (s, 2H), 7.33 (br s, 2H), 7.85 (s, 4H).

Employing the procedure substantially as described in Example 3, but substituting for the 4-bromophenylthiomethanesulfonamide used therein, the thiomethanesulfonamides described in Table II there were produced the sulfonylmethanesulfonamides also described in Table II in accordance with the following reaction scheme:

TABLE II $$R^1S-\underset{R^3}{\underset{|}{\overset{R^2}{\overset{|}{C}}}}-SO_2NH_2 \longrightarrow R^1-SO_2-\underset{R^3}{\underset{|}{\overset{R^2}{\overset{|}{C}}}}-SO_2NH_2$$

| R$^1$ | R$^2$ | R$^3$ | m.p. (°C.) |
|---|---|---|---|
| 4-HOC$_6$H$_4$— | H | H | 206–208 |
| 4-CH$_3$OC$_6$H$_4$CH$_2$— | H | H | 189.5–191.0 |
| C$_6$H$_5$CH$_2$CH$_2$— | H | H | 184–186 |
| C$_6$H$_5$(CH$_2$)$_3$— | H | H | 140–141 |
| 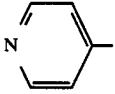 | H | H | 210 (dec.) |
| 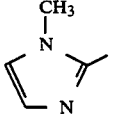 | H | H | 197 (dec.) |
| n-C$_8$H$_{17}$ | H | H | 136–138 |

EXAMPLE 4

4-(3-hydroxypropylthio)phenylsulfonylmethanesulfonamide

A suspension of 1.3 g of a 60% sodium hydride/oil dispersion was prepared in 30 ml of dry DMF under an atmosphere of nitrogen. 3-Mercaptopropanol (2.5 ml) was added dropwise to the above suspension. When gas evolution and frothing had ceased 7.3 g of 4-bromophenylsulfonylmethanesulfonamide was added and the resulting thick slurry was heated to 80° C. After 2 hours all solid had dissolved. The reaction mixture was heated at 80° C. for 10 hours, then cooled to room temperature, and 6 ml of 6N hydrochloric acid was added. Mineral oil was extracted out with hexane. Water (750 ml) then was added to the DMF causing a solid to precipitate. The solid was filtered and dried under vacuum at 85° C. The solid was dissolved in hot ethyl acetate, treated with decolorizing charcoal, and filtered while hot. Upon cooling the product crystallized. Yield 3.9 g (52.0%). NMR (DMSO-d$_6$, 90 MHz) δ 1.8 (m, 2H), 3.1 (t, 2H), 3.5 (t, 2H), 5.06 (s, 2H), 7.26 (s, 2H), 7.45 (d, 2H), 7.80 (d, 2H). m.p. 150°–151° C. (Found: C, 36.61; H, 4.47; N, 4.24. C$_{10}$H$_{15}$NO$_5$S$_3$ requires C, 36.91; H, 4.65; N, 4.30%).

Employing the procedure substantially as described in Example 4, but substituting for the 3-mercaptopropanol used therein, an equimolar amount of 2-mercaptoethanol, there was produced in comparable yield 4-(2-hydroxyethylthio)phenylsulfonylmethanesulfonamide, m.p. 136°–137° C.

EXAMPLE 5

4-(3-hydroxypropylsulfonyl)phenylsulfonylmethane sulfonamide

To a solution of 1.9 g of 4-(3-hydroxypropylthio)-phenylsulfonyl methane sulfonamide in hot water was added dropwise an aqueous solution of 7.2 g of Oxone$^R$. When addition was completed the reaction mixture was cooled to room temperature and the solid present was filtered. The solid was washed with water and air dried. The solid was recrystallized from methanol. Yield 1.7 g (82% yield). NMR (DMSO, d$_6$, 90 MHz) δ 1.66 (m, 2H), 3.35 (m, 4H), 5.30 (s, 2H), 7.40 (s, 2H), 8.18 (m, 4H). m.p. 200°–200.5° C. (Found: C, 33.56; H, 4.13; N, 3.88. C$_{10}$H$_{15}$NO$_7$S$_3$ requires C, 33.60; H, 4.23; N, 3.92%).

4-2-(Hydroxyethylsulfonyl)phenylsulfonylmethanesulfonamide, m.p. 198.5°–200.0° C. was prepared similarly from the corresponding hydroxyethylthio compound.

EXAMPLE 6

2-Thienylthiomethanesulfonamide

Thiophene (6.9 ml) and 75 ml of ether were mixed under an atmosphere of nitrogen. n-Butyl lithium (60 ml, 1.6M in hexane) was added dropwise and the mixture was refluxed for 1 hour. The reaction mixture was cooled to −65° C. and 2.8 g of elemental sulfur was added. The reaction mixture was stirred at −70° C. for 45 minutes and then allowed to warm to room temperature. The ether solvent was removed under vacuum and 50 ml of dimethylformamide was added. Bromomethanesulfonamide (15 g) was added and the reaction mixture was heated to 80° C. After 1.5 hours at 80° C. the reaction mixture was cooled to room temperature and the DMF was removed under vacuum. Hydrochloric acid (1N) and ethyl acetate were added to the oily residue. The ethyl acetate phase was separated and washed with brine, dried over sodium sulfate and concentrated under vacuum. The resultant oil was chromatographed using 230–400 mesh silica gel and eluting with 1:1 ethyl acetate:hexane. Yield 11.3 g of solid (62.8%). N.M.R. (CDCl$_3$, 300 MHz) δ 4.26 (s, 2H), 5.13 (brs, 2H), 7.02 (m, 1H), 7.38 (m, 1H), 7.46 (d, 1H).

EXAMPLE 7

5-(3-Hydroxypropylthio)thien-2-ylsulfonylmethanesulfonamide

Step A: Preparation of N,N-dimethyl-5-bromothien-2-ylsulfonylmethanesulfoformamidine A solution of 11.0 g of 2-thienylthiomethanesulfonamide in 200 ml of acetonitrile was prepared and 9.1 ml (1.3 equivalents) of dimethylformamide dimethylacetal added. After stirring at room temperature for 30 minutes the reaction mixture was concentrated under vacuum. The resultant solid residue was dissolved in warm benzene and 9.4 g of N-bromosuccinimide was added. After stirring at room temperature for 30 minutes the benzene solution was extracted with aqueous sodium bisulfite. A subsequent wash with distilled water caused a solid to precipitate out in the separatory funnel. This solid was filtered and the benzene layer was separated from the filtrate, dried over sodium sulfate and concentrated under vacuum to give 16.2 g of solid. This solid was dissolved in cold methanol and an aqueous solution of 58 g of Oxone$^R$ was added. After stirring for four hours the solid product was isolated by filtration. This solid was suspended in boiling water to dissolve any inorganics present and after cooling to room temperature the solid was filtered and dried at 65° C. under vacuum. Yield 11.6 g (58.8%). N.M.R. (DMSO, d$_6$, 300 MHz) δ 2.84 (s, 3H), 3.13 (s, 3H), 5.37 (s, 2H), 7.46 (d, 1H), 7.66 (d, 1H), 7.95 (s, 1H).

Step B: Preparation of 5-(3-hydroxypropylthio)thien-2-ylsulfonylmethanesulfonamide, 7

A 60% sodium hydride/oil dispersion (1.8 g) was washed twice with hexane to remove mineral oil. The sodium hydride was placed under vacuum to remove any residual hexane. It was then placed under an atmosphere of nitrogen. Dimethyl formamide (50 ml) was added, the mixture was cooled to 0° C. and 3.6 ml of 3-mercaptopropanol was added dropwise. When gas evolution and frothing had ceased 12.5 g of N,N-dimethyl-5-bromothien-2-ylsulfonylmethanesulfoformamidine was added and the cold bath removed. The reaction mixture was heated to 80° C. and maintained there for 3 hours. The reaction mixture was concentrated under vacuum and the residue dissolved in 100 ml of methanol. Ten percent aqueous sodium hydroxide (100 ml) was added and the mixture was heated for 1-hour with a hot water bath. The reaction mixture was concentrated under vacuum to remove methanol. After cooling, 6N hydrochloric acid was added until the mixture was neutral. A solid which precipitated was extracted into ethyl acetate. The ethyl acetate was separated, dried over sodium sulfate and concentrated under vacuum. The oily residue was triturated with dichloroethane causing crystallization. The solid was recrystallized from water with charcoal added and filtered hot. Yield 4.9 g (44.5%) m.p. 92.5°–93.0° C. N.M.R. (DMSO-d$_6$, 300 MHz) δ 1.73 (m, 2H), 3.06 (t, 2H), 3.46 (t, 2H), 5.22 (s, 2H), 7.22 (d, 1H), 7.40 (s, 2H), 7.72 (d, 1H). Found: C, 28.86; H, 3.85; N, 3.94. C$_8$H$_{13}$NO$_5$S$_4$ requires C, 28.99; H, 3.95; N, 4.22%.

EXAMPLE 8

5-(4-Hydroxybutyl)thien-2-ylsulfonylmethane sulfonamide

Step A: Preparation of 4-thien-2-yl butanol

A solution of 10.0 g of 4-thien-2-ylbutyric acid in 50 ml of dry THF was prepared under an atmosphere of nitrogen. The solution was cooled to 0° C. and 59 ml of diborane in THF was added dropwise. When addition was complete the reaction mixture was stirred at room temperature for 30 minutes then water was added until a solid began to precipitate. The reaction mixture was concentrated under vacuum and 1N hydrochloric acid was added to the liquid-solid residue until dissolution occured. The solution was extracted with ethyl acetate, then the ethyl acetate phase was washed with aqueous sodium carbonate then with brine. The ethyl acetate phase was dried over sodium sulfate then concentrated under vacuum to give mostly an oil residue. The oil was pipetted away from a small amount of solid and placed under high vacuum to remove any traces of solvent. Yield 7.86 g of oil (85.4%). N.M.R. (CDCl$_3$, 300 MHz), δ 1.60 (m, 2H), 1.72 (m, 2H), 2.64 (s, 1H), 2.85 (t, 2H), 3.62 (t, 2H), 6.80 (d, 1H), 6.92 (m, 1H), 7.10 (d, 1H).

Step B: Preparation of 5-(4-hydroxybutyl)thien-2-yl sulfonylmethanesulfonamide A solution of 7.8 g of 4-thien-2-ylbutanol in methylene chloride was prepared and a catalytic amount of toluenesulfonic acid added, followed by dropwise addition of 4.8 ml of dihydropyran. When thin layer chromatography indicated a completed reaction (20 minutes), the reaction mixture was extracted with aqueous sodium carbonate. The organic layer was separated, dried over sodium sulfate and concentrated under vacuum to give 10.1 g of oil residue. This oil was dissolved in 50 ml of ether and placed in a flask under an atmosphere of nitrogen. The solution was cooled to 0° C. and 28 ml of 1.6N butyl lithium in hexane was added dropwise. The cold bath was removed and the reaction mixture stirred at room temperature for 45 minutes. The reaction mixture was cooled to −60° C. and 1.36 g of sulfur added. After 30 minutes of stirring at −60° C. the reaction mixture was allowed to warm to room temperature, the ether was decanted from a gummy solid which had formed and dimethylformamide was added as a replacement solvent. Bromomethanesulfonamide (7.3 g) was added and the reaction mixture was heated to 80° C. After one hour at 80° C. the reaction mixture was allowed to cool to room temperature. The reaction mixture was concentrated under vacuum to give a thick oil residue. The residue was treated with 1N aqueous sodium hydroxide to remove any sulfonamides present. The hydroxide solution was washed with ether several times until the ether wash was colorless. The hydroxide solution was cooled to 10° C. and 6N hydrochloric acid added in order to bring the pH to 8.5. A gummy solid was extracted using ethyl acetate and the ethyl acetate was filtered through a small amount of silica gel, washing the silica gel with ethyl acetate. The ethyl acetate was concentrated under vacuum to give 5.7 g of oil residue. This oil was dissolved in methanol and an aqueous solution of 19.2 g of Oxone$^R$ added. After heating at 40° C. for 3 hours the mixture was brought to a boil then allowed to cool. The methanol was removed under vacuum and the aqueous residue was extracted with ethyl acetate. The ethyl acetate was dried over sodium sulfate then concentrated under vacuum to give 5.1 g of oil residue. This oil was chromatographed using 230–400 mesh silica gel and eluting with 45% hexane:45% ethyl acetate:10% methanol. When product fractions were combined and concentrated under high vacuum 2.8 g of liquid product was obtained which was still impure. This oil was dissolved in hot dichloroethane, treated with charcoal and filtered. The filtrate was concentrated somewhat then cooled to −10° C. A solid was obtained upon scratching. Since the solid still gave a poor HPLC analysis it was rechromatographed, this time eluting with 5% methanol in chloroform. When product fractions were combined and concentrated under high vacuum a waxy solid was obtained. m.p. 79°–80° C. N.M.R. (CDCl$_3$, 300 MHz) δ 1.62 (m, 2H), 1.80 (m, 2H), 2.92 (m, 3H), 3.62 (t, 2H), 4.86 (s, 2H), 6.68 (br s, 2H), 6.90 (d, 1H), 7.70 (d, 1H). (Found: C, 34.86; H, 4.92; N, 3.94%. C$_9$H$_{15}$NO$_5$S$_3$ requires C, 34.49; H, 4.82; N, 4.47%).

EXAMPLE 9

4-Butanoyloxyphenylsulfonylmethanesulfonamide 4-hydroxyphenylsulfonylmethanesulfonamide (0.4 g) was dissolved in 12 ml of tetrahydrofuran. Pyridine (0.15 ml) was added to the solution followed by 0.30 ml of butyric anhydride. The mixture was stirred overnight at room temperature then the solvent was removed under vacuum. The solid thus obtained was washed with water, filtered, and dried under vacuum at 60° C. The solid was recrystallized twice from dichloroethane. m.p. 160°-161° C. N.M.R. (DMSO, $d_6$); δ 0.97 (t, 3), 1.68 (q, 2), 2.56 (t, 2), 5.22 (s, 2), 7.43 (s, 2 overlapping d, 2), 8.02 (d, 2). Anal. Calc'd for $C_{11}H_{15}NO_6S_2$: C, 41.11; H, 4.71; N, 4.36; M.W. 321.36. Found: C. 41.01; H. 4.66; N, 4.25.

EXAMPLE 10

4-Methoxyphenylmethylsulfinylmethanesulfonamide

4-Methoxyphenylmethylthiomethanesulfonamide was prepared by alkylation of 4-methoxybenzylthiol with bromomethane sulfonamide by the procedures described in Example 2. Sodium metaperiodote (0.8 g) was dissolved in water and added to a methanolic solution of the sulfide (0.6 g). A solid gradually precipitated as the mixture stirred at room temperature. The solid was filtered and set aside. The filtrate was concentrated under vacuum and the residue obtained was treated with ethyl acetate and a solid filtered. This solid was combined with the above solid and recrystallized from water. Yield 63%. m.p. 186°-187° C. N.M.R. (DMSO, $d_6$); δ 3.73 (s, 3), 4.10 (d, 1), 4.14 (d, 1), 4.26 (d, 1), 4.53 (d, 1), 6.93 (m, 2), 7.23 (m, 4). Anal Calc'd for $C_9H_{13}NO_4S_2$: C, 41.05; H, 4.98; N, 5.32; M.W. 263.33. Found: C, 40.85; H, 4.87; N, 5.37.

Prepared also by the same method were 2-phenylethylsulfinylmethanesulfonamide and 3-phenylpropylsulfinylmethanesulfonamide.

EXAMPLE 11

Octylsulfonylchloromethanesulfonamide

Octylthiomethanesulfonamide (5.9 g) was dissolved in tetrahydrofuran and cooled to −70° C. A solution of meta-chloroperbenzoic acid (5.3 g) in tetrahydrofuran was added dropwise. When addition was complete a precipitate was isolated by filtration. A second crop of solid was obtained by concentrating the filtrate under vacuum. This second crop of solid was treated with aqueous sodium carbonate and filtered. After drying the combined yield of both crops of solid was 5.4 g. This solid was suspended in methylene chloride (250 ml) and thionyl chloride (2.4 ml) was added. After 3 hours of reflux the cooled reaction mixture was extracted with aqueous sodium bicarbonate. The methylene chloride layer was dried over sodium sulfate and concentrated under vacuum, yielding 6.2 g of oil. This oil was dissolved in tetrahydrofuran and after cooling with an ice bath a solution of meta-chloroperbenzoic acid (10.1 g) in tetrahydrofuran was added. The reaction mixture was allowed to warm to room temperature and was stirred for 16 hours. The reaction mixture was concentrated under vacuum. The residue obtained was dissolved in ether and extracted with aqueous sodium carbonate and then with brine. After drying over sodium sulfate the ether phase was concentrated under vacuum to yield 2.5 g of solid. This solid was chromatographed to give 0.42 g of desired product. m.p. 73°-74° C. 'H NMR (CDCl$_3$) δ 0.89 (t, 3H), 1.30 (m, 10H), 1.92 (m, 2H), 3.52 (m, 2H), 5.57 (s, 1H). Analysis calc'd for $C_9H_{20}ClNO_4S_2$: C, 35.34; H, 6.59; N, 4.58. Found: C, 35.72; H, 6.75; N, 4.81.

EXAMPLE 12

N-(1-Heptyl)methanedisulfonamide

Step A: Preparation of N-(1-Heptyl)methanesulfonamide

A solution of 7.5 ml (50 mmol) of n-heptylamine in 50 ml of THF was cooled in an ice-water bath. Methanesulfonyl chloride (1.93 ml, 25 mmol) was added dropwise, with stirring to the amine solution over a 4 minute period. After stirring for an additional 45 minutes the mixture was poured into dilute HCl, and the product was extracted with ethyl acetate. The extract was washed with brine, dried (Na$_2$SO$_4$) and evaporated in vacuo. The resulting yellow solid was recrystallized from hexane. Yield: 4.03 gm. 'H-NMR (CDCl$_3$) δ 4.48 (1H, br t); 3.13 (2H, q, J=6H$_2$); 2.96 (3H, s); 1.57 (2H, m); 1.30 (8H, br m); 0.89 (3H, br t).

Step B: Preparation of N-(1-heptyl)methanedisulfonamide

A solution of the product of Step A (2.05 g, 10.6 mmol) and 5 mg of bipyridyl was prepared in 20 ml of THF, and the solution was cooled to −70° C. A solution of n-butyl lithium in hexane (14 ml, 22 mmol) was added to the cold mixture over a 5 minute period. After stirring at −70° C. for 1 hour, the mixture was allowed to warm to −10° C. over a 20 minute period. After re-cooling to −70° C., sulfur dioxide gas was introduced into the reaction vessel until the solution became nearly colorless. Acetic acid (0.64 ml) and hexane (50 ml) were added sequentially and the resulting suspension was allowed to warm to room temperature. The solid product was isolated by filtration. The hygroscopic salt was suspended in water. Sodium acetate trihydrate (2.6 gm) and hydroxylamine-O-sulfonic acid (1.35 gm, 11.9 mmol) were added and the mixture was stirred at room temperature overnight. The product was extracted into ethyl acetate and the extract was washed with brine and dried (Na$_2$SO$_4$). Evaporation gave 1.25 g of an off-white solid. Recrystallization from dichloroethane/acetone gave 0.83 gm of material which was dissolved in 0.25N NaOH solution. The solution was washed with ether and then acidified (HCl). The precipitated product was isolated by filtration. After drying, 0.69 gm of a white solid, mp 174°-177° C., was obtained. 'H-NMR (acetone-d$_6$): δ 6.46 (2H, br s); 6.33 (1H, br t); 4.76 (2H, s); 3.17 (2H, q, J=6 Hz); 2.60 (2H, m); 1.30 (8H, br m); 0.86 (3H, br t). Analysis Calc'd for $C_8H_{20}N_2O_4S_2$ (MW=272.506): N, 10.28; C, 35.26; H, 7.40. Found: N, 10.58; C, 35.22; H, 7.13.

Employing the procedures substantially as described in Example 12, there were prepared:
N-(2-methylprop-2-yl)methanedisulfonamide (mp=162°-164° C.); and
N-(3-morpholinylprop-1-yl)methanedisulfonamide (mp=171°-173° C.)

What is claimed is:

1. A compound of structural formula:

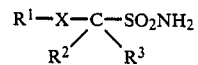

wherein
X is $SO_2$
$R^1$ is
(a) thienyl, either unsubstituted or substituted with one or more of:
 (i) $R^5$, which is $C_{1-5}$ alkyl, either straight or branched chain either unsubstituted or substituted with one or more of —$OR^4$, wherein $R^4$ is hydrogen, $C_{1-3}$ alkyl, or $C_{2-4}$ alkanoyl,
 (ii)

wherein n is 0, 1 or 2 and $R^5$ is as defined above
(b) $C_{1-8}$ alkyl either straight chain or branched chain, and either unsubstituted or substituted with
 (i) carbocyclic or heterocyclic aromatic such phenyl, naphthyl, pyridyl, thienyl, imidazolyl or quinolinyl, either unsubstituted or substituted with:
  (1) $OR^4$ or
  (2) $R^5$; wherein $R^4$ and $R^5$ are as defined above $R^2$ is hydrogen, and $R^3$ is hydrogen, chloro, or fluoro.

2. The compound of claim 1 wherein $R^1$ is $C_{1-8}$ alkyl and $R^3$ is hydrogen or chloro.

3. The compound of claim 2, wherein $R^3$ is chloro.

4. The compound of claim 3, wherein $R^1$ is alkyl.

5. A method of treating elevated intraocular pressure and glaucoma which comprises the administration to a patient in need of such treatment an effective intraocular pressure lowering amount of the compound of claim 1.

6. The method of claim 5, wherein $R^1$ is $C_{1-8}$ alkyl and $R^3$ is hydrogen or chloro.

7. The method of claim 6, wherein $R^3$ is chloro.

8. An ophthalmological composition for the treatment of elevated intraocular pressure and glaucoma comprising an ophthalmologically acceptable carrier and an effective intraocular pressure lowering amount of the compound of claim 1.

9. The composition of claim 8, wherein $R^1$ is $C_{1-8}$ alkyl and $R^3$ is hydrogen or chloro.

10. The composition of claim 9, wherein $R^3$ is chloro.

* * * * *